United States Patent [19]

Young

[11] 4,230,108

[45] Oct. 28, 1980

[54] APPARATUS AND METHOD FOR SEALING ESOPHAGEAL ENTRANCE TO TRACHEA ABOVE AND BELOW

[76] Inventor: Sharon L. Young, 8600 Pontchartrain Blvd. Apt. 312, New Orleans, La. 70124

[21] Appl. No.: 20,146

[22] Filed: Mar. 13, 1979

[51] Int. Cl.³ .......................................... A61M 25/00
[52] U.S. Cl. ............................ 128/207.15; 128/349 B
[58] Field of Search ............................... 128/348–351, 128/207.14, 207.15

[56] References Cited

U.S. PATENT DOCUMENTS

| | | | |
|---|---|---|---|
| 2,175,726 | 10/1939 | Gebauer | 128/349 B |
| 2,981,254 | 4/1961 | Vanderbilt | 128/349 B |
| 4,090,518 | 5/1978 | Elam | 128/207.15 |

Primary Examiner—Dalton L. Truluck
Attorney, Agent, or Firm—James B. Lake, Jr.

[57] ABSTRACT

A flexible esophageal tube is provided for insertion through the mouth, downward past the tracheal entrance and into the esophagus to a lower limit opposite the tracheal carina. Inflatable cuffs are respectively fixed, above and below the tracheal entrance, on the esophageal tube for sealing the tracheal entrance against leakage around the tube. A ventilating tube is sealed in the esophageal tube against the anterior wall of the upper part thereof with an open distal end projecting out of the esophageal tube and mouth and a closed distal end extending past the tracheal entrance. Perforations defined in the common anterior surface of both tubes between the cuffs admits anesthetics, introduced at the distal end of the ventilating tube, to pass into the tracheal entrance, trachea and lungs. Thus there can be no mixing of vomit expelled from the stomach through the esophageal tube with general anesthetic and air forced into ventilating tube and the esophagus between inflated cuffs and destined for trachea and lungs.

2 Claims, 3 Drawing Figures

APPARATUS AND METHOD FOR SEALING ESOPHAGEAL ENTRANCE TO TRACHEA ABOVE AND BELOW

BACKGROUND OF THE INVENTION

The invention relates generally to esophageal tubes and more particularly to an integral combination of tubes for respectively passing vomit from the stomach and air and anesthetic to and from the trachea with no intermixing.

In the administering of anesthetics there is always the danger of nauseating the recipient to cause vomiting. Any entrance of vomit into the lungs causes damage and maybe death, and therefore must be prevented. It is not always feasible to stop anesthesia during an operation, or even possible, and thereby ensure no vomit enters the recipient's lungs. The invention ensures the same result while continuing the anesthesia.

The prior art comprises endo-tracheal tubes and catheters that obstruct the mouth and pharynx and the free passage of vomit therethrough. Cuffs on endo-tracheal tubes are expanded at such low pressure for the prevention of necrosis and, because the alternating respiratory forces are low, there is no assurance that the much greater vomiting forces will not force vomit past endo-tracheal cuffs. See the following U.S. Pats. Goodyear, Nos. 3,731,692; McGinnis, 3,642,005; Sheridan, 3,605,750 and 3,625,793; Harautuneian 3,848,605; Basil, 3,884,242; Puig 3,481,339; Baran, 3,173,418; Jackson, 3,766,927 and 3,854,484; and Igich, 4,119,101.

A U.S. Pat. No. to Hewson et al, 3,905,361 for Apparatus For Sealing The Esophagus And Providing Artificial Respiration And Evacuating The Stomach is more in point. The differences with the invention comprises restrictive esophageal tube openings and a smaller esophageal tube adapted for use with stomach evacuator and to allow an additional endo-tracheal tube to be inserted in the trachea. Also a mask has been substituted for an upper cuff and that permits the tongue to close the pharynx against the entrance of air and anesthetic which requires removal of the face mask to correct and the possible entry of vomit through the unsealed nose and mouth. An article, The Esophgeal Obturator Airway, published in Chest 69: L Jan. 1976 issue describes similar apparatus except that the esophagus is plugged below the tracheal entrance and the esophageal tube is perforated at that area. Such plugging of the esophagus could cause the rupture thereof or of the stomach in case of naseau. Any of the foregoing unhappy ocurrences may result in a suit for malpractice and is a cause of anxiety to anesthetists.

SUMMARY OF THE INVENTION

It is an object of the invention to provide individual passageways from beyond the mouth to the stomach and trachea entrance, said passage-ways being sealed from each other for the positive prevention of any stomach contents or vomit entering the lungs.

Another object of the invention is to seal the pharynx and the esophagus respectively above and below the tracheal entrance without exerting pressure toward or against the trachea.

Still another object of the invention is to provide a method of simultaneously administering general anesthesia to the trachea while the patient is vomiting and without endangering his life.

DESCRIPTION OF THE PREFERRED EMBODIMENT

Figures 1, 2, 3:
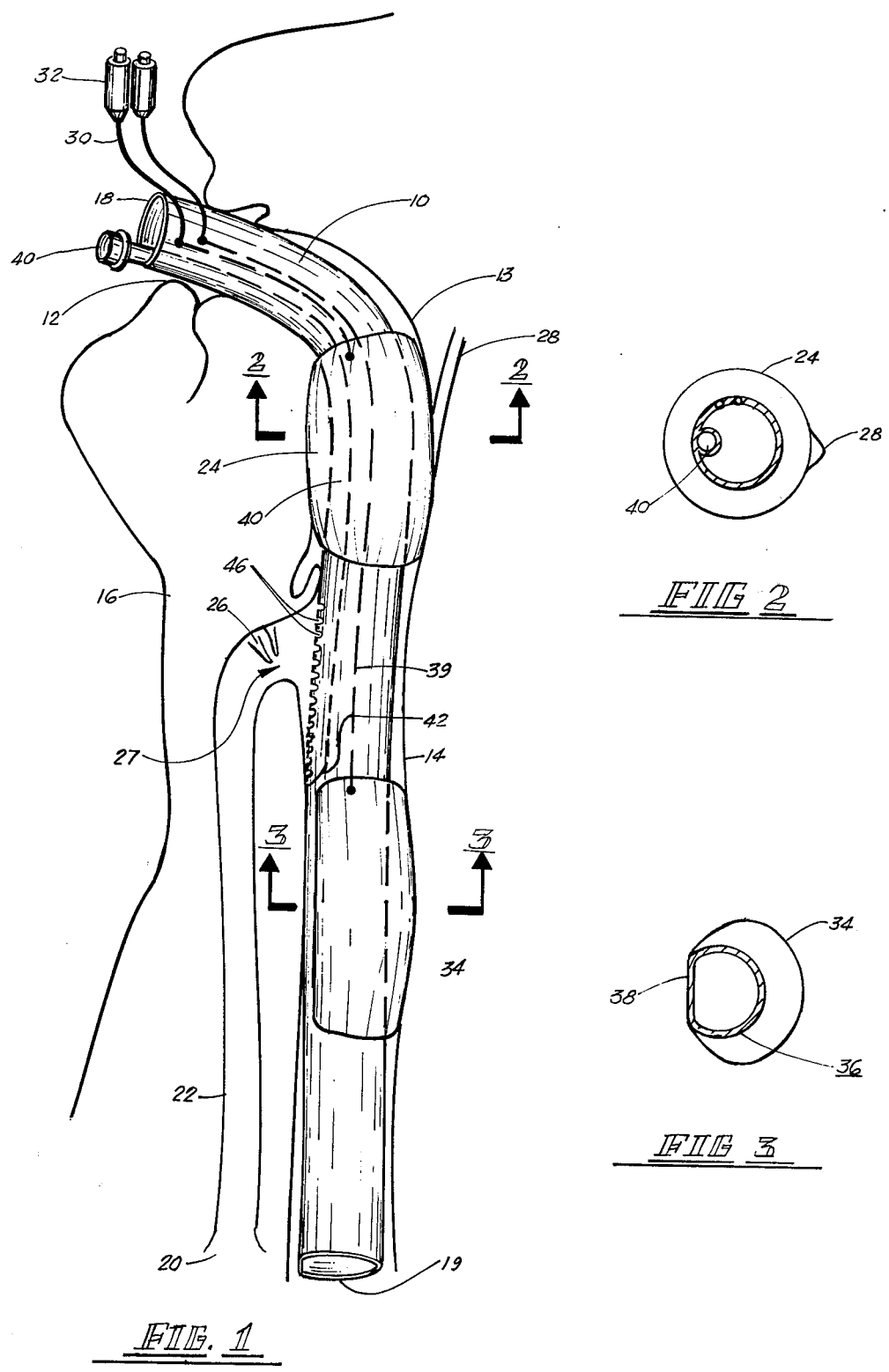
FIG. 1 is a side elevational view of the invention shown in operating position against a facial outline.
FIG. 2 is a cross-section taken along section lines 2—2 of FIG. 1.
FIG. 3 is similar to FIG. 2 but taken along section lines 3—3 of FIG. 1.

Referring to FIGS. 1—3, the invention comprises a flexible tube 10 for insertion through the mouth 12 and pharynx 13 and into the esophagus 14. Tube 10 has two oppositely disposed open ends 18 and 19 respectively, and extends from outside the mouth 12 to a place in the esophagus opposite carina 20 of trachea 22. An upper cuff 24 is mounted around tube 10 above vocal chords 26 and tracheal entrance 27 and blocks nasopharynx 28. A duct 30, with inflating and deflating fittings 32, is fixed in and to tube 10 for use with cuff 24. A lower cuff 34 is mounted partially around tube 10 on posterior side 36 and below tracheal entrance 27, at which point tube 10 is flattened on its anterior side 38 to end 19. Said side 38 seals with the esophagus by pressure of the expanded lower cuff 34 on its posterior side 36. By this arrangement possibility of compressing trachea 22 is eliminated. Cuff 34 is also provided with fitting 32 and an inflating duct 39 similar to those of cuff 24. By using two cuffs no removable mask is required to seal the nose and mouth against vomit and escape of anesthetics.

A ventilation tube 40 is fixed in the upper part of tube 10 along its anterior side to extend from outside the mouth and beyond end 18 to a closed end 42 on the far side of tracheal entrance 27. Both tubes 10 and 40 define common perforations 46 opposite said tracheal entrance and between cuffs 24 and 34 for the only connections therebetween, the perforations not extending into the interior passageway defined between tubes 10 and 40. By using two nested tubes, rather than one tube and the passage defined between said tube and the pharynx, the tongue is prevented from closing the anesthetic and air passage to the trachea.

In operation, tube 10, in which tube 40 is fixed, is inserted through the mouth, laryngeal pharynx and into the esophagus as shown in FIG. 1. Cuffs 24 and 34 are inflated through their respective ducts and fittings to seal off the tracheal entrance 27 from any leakage from around tube 10 from above or below and closing these entrances to the trachea. Anesthesia is administered through tube 40 and out perforations 46 to the trachea entrance and lungs (not shown). Should the recipient become nauseated, vomit freely exits through tube 10, where it is sealed from perforations 46, and out end 18 clear of the mouth.

What is claimed is:

1. Apparatus for sealing trachea entrance from above and below entrance to esophagus comprising:
 (a) flexible esophageal tube means, having oppositely disposed ends, for insertion of one end into the esophagus past the entrance of said trachea to a position in the esophagus opposite tracheal carina, with the other end remaining outside of the mouth, said esophagus tube means being flattened on a anterior side thereof between said trachea entrance and carina for sealing said esophageal tube means on an area greater than a tangential strip;

(b) upper inflatable cuff means fixed to said esophageal tube means above said tracheal entrance for sealing said tracheal entrance from above;

(c) lower inflatable and deflatable cuff means fixed between said trachea entrance and above said tracheal carina said lower cuff means extending around the round posterior sides only and providing no expansion on the flattened anterior side to possibly occlude said trachea in case of over inflation of said lower cuff; and (d) ventilation tube means, having an open end and closed end, interiorly fixed to an anterior side of said esophageal tube means, said anterior side being common to both said tube means, and with said open end extending outwardly beyond the mouth of said esophageal tube means, and the closed end extending past said tracheal entrance, said common anterior side defining perforations opposite said entrance for ventilating the lungs therethrough.

2. Method of sealing trachea entrance from above and below entrance to esophagus comprising the steps of:

(a) inserting an esophageal tube through the mouth, past the tracheal entrance and into the esophagus as far as opposite the tracheal carina, for providing a through passage past said tracheal entrance;

(b) sealing the space between the pharynx, the esophagus, and the esophageal tube with inflatable and deflatable cuffs, above and below the tracheal entrance during the period of anesthesia for preventing any leakage from above, below and around said tube, when said cuffs are inflated, into said sealed space;

(c) flattening the anterior side of said esophageal tube below tracheal entrance for sealing along a broader area than a tangential strip;

(d) restricting lower inflatable cuff to posterior side of the esophageal tube for preventing occlusion of trachea by overinflation of said inflatable lower cuff; and (e) providing a ventilating tube for passing anesthetic and air into said sealed space, said ventilating tube being fixed to the anterior side of said esophageal tube and common therewith, said common side being perforated to open solely into said sealed space, whereby anesthetic and air passing into said sealed space and vomit passing therearound are sealed apart.

* * * * *